United States Patent [19]
Zepf

[11] Patent Number: 5,624,389
[45] Date of Patent: Apr. 29, 1997

[54] KNEE JOINT ORTHOSIS

[75] Inventor: Armin Zepf, Duderstadt, Germany

[73] Assignee: Otto Bock Orthopadische Industrie Besitz-Und Verwaltungs-Kommanditgesellschaft, Duderstadt, Germany

[21] Appl. No.: 439,379

[22] Filed: May 11, 1995

[30] Foreign Application Priority Data

May 30, 1994 [DE] Germany .......................... 44 18 806.4

[51] Int. Cl.[6] .................................................... A61F 5/01
[52] U.S. Cl. .................................. 602/26; 602/16
[58] Field of Search ................... 602/16, 23, 26, 602/5

[56] References Cited

U.S. PATENT DOCUMENTS

| | | |
|---|---|---|
| 3,026,869 | 3/1962 | Peach . |
| 3,799,159 | 3/1974 | Scott ...................... 602/16 X |
| 4,617,920 | 10/1986 | Carsalade ................ 602/26 X |
| 4,873,967 | 10/1989 | Sutherland ................ 602/26 |
| 4,958,643 | 9/1990 | Pansiera ................ 602/26 |
| 4,961,416 | 10/1990 | Moore et al. ............... 602/16 |
| 4,966,133 | 10/1990 | Kausek . |
| 5,018,514 | 5/1991 | Grood et al. . |
| 5,201,776 | 4/1993 | Freeman ................ 602/26 X |
| 5,316,547 | 5/1994 | Gildersleeve ............ 602/26 X |
| 5,352,190 | 10/1994 | Fischer et al. ........... 602/26 |
| 5,399,149 | 3/1995 | Frankowiak et al. ....... 602/26 |
| 5,472,412 | 12/1995 | Knoth ................... 602/26 X |

FOREIGN PATENT DOCUMENTS

| | | |
|---|---|---|
| 44228B | 1/1990 | Austria . |
| 0567673A1 | 4/1992 | European Pat. Off. . |
| 1055177 | 4/1959 | Germany . |
| 3825813A1 | 2/1990 | Germany . |

*Primary Examiner*—Richard J. Apley
*Assistant Examiner*—David R. Risley
*Attorney, Agent, or Firm*—Whitham, Curtis, Whitham & McGinn

[57] ABSTRACT

The invention relates to a knee joint orthosis with a thigh shell (2) fastenable to thigh (1) of the patient with bandages or the like, a lower leg shell (4) likewise fastenable by bandages or the like to lower leg (3), and with two joint rods (5), said rods being located laterally opposite one another, approximately parallel with the leg extended, and connecting the two leg shells (2, 4) with one another with articulation, each of said rods being operatively connected at its upper end by an upper articulation point (8) with thigh shell (2) and at its lower end by a lower articulation point (10) with lower leg shell (4) in such manner that the distance between the two articulation points (8, 10) decreases from a maximum with the leg extended to a minimum with the knee completely flexed. To simplify the design and the operation, it is proposed according to the invention that the pivoting of at least one joint rod (5) around its lower articulation point (10) from the extended leg position into a knee bend take place against a force opposing the pivoting, said force increasing up to a knee bend of about 30° to 40° and decreasing once again with an approximately 90° bend (seated position).

15 Claims, 5 Drawing Sheets

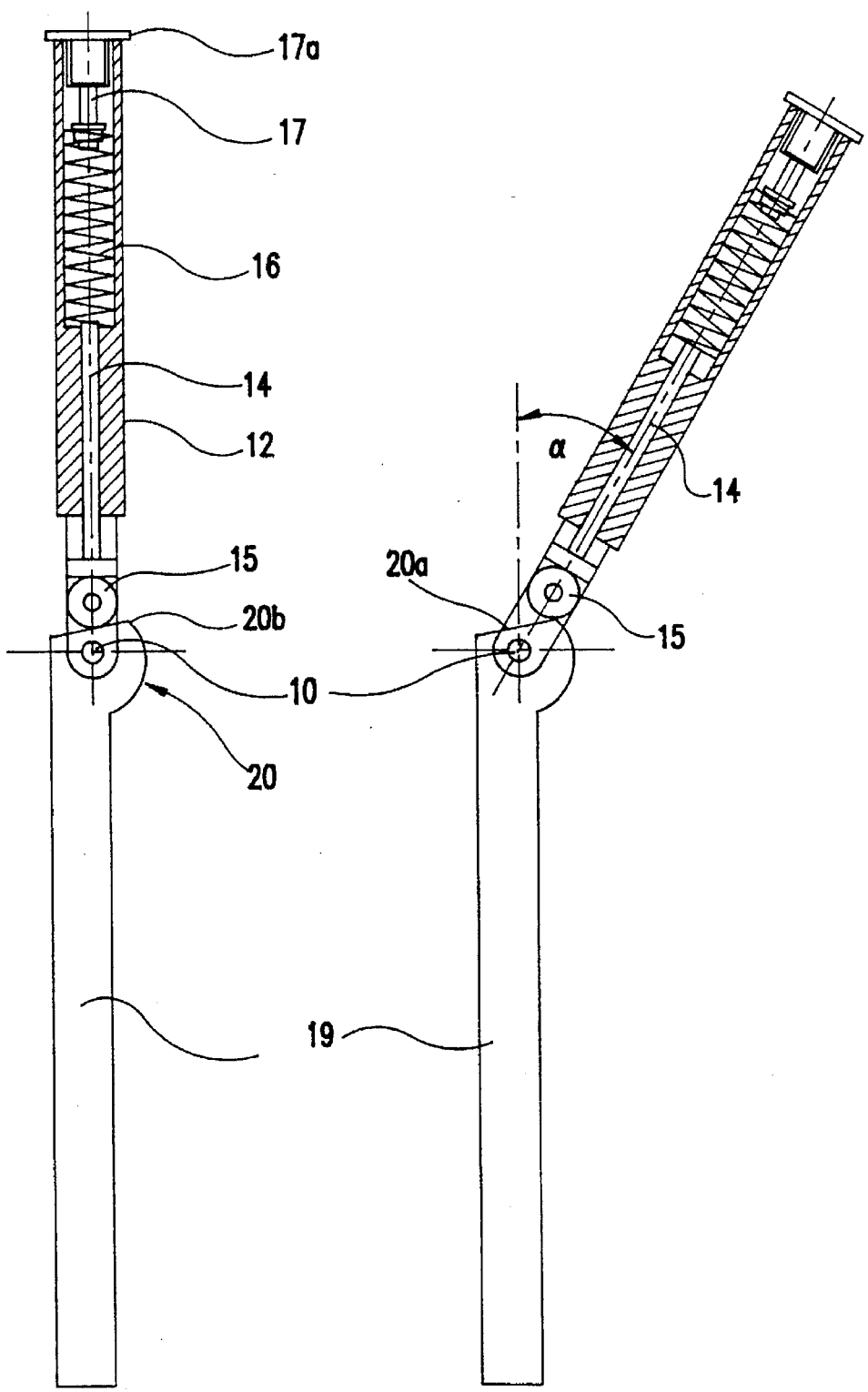

KNEE JOINT ORTHOSIS

BACKGROUND OF THE INVENTION

1. Field of the Invention

The invention relates to a knee joint orthosis with a thigh shell to be attached to the patient's thigh, a lower leg shell to be attached likewise by bandages or the like to the lower leg, and with two joint rods, said rods being located laterally opposite one another, approximately perpendicular with the leg extended, and connecting the two leg shells together with articulation, each of said rods being connected at its upper end by an upper articulation point with the thigh shell and at its lower end by a lower articulation point with the lower leg shell in such fashion that the distance between the two articulation points decreases from a maximum with the leg extended to a minimum with the knee completely flexed.

2. Description of the Prior Art

EP 0 567 673 A1 shows an embodiment wherein each of the two joint rods is made adjustable lengthwise in telescopic fashion. In addition, a device is provided for dorsal flexion of the lower leg by means of the backward displacement of the joint rods, said device being formed by a ventral elastic torsion bar guided around the lateral joint rods. Each joint rod consists of two telescoping rods guided one inside the other in telescopic fashion, said rods being connectable with one another by an inner rubber cord. The two lower articulation points of the joint rods are connected together by a dorsal shackle.

An important feature of this known orthosis lies in the fact that no mechanical joint simulating the individual knee joint mechanics is provided. Instead, the knee joint mechanics are given free rein to perform the physiological movement unimpeded. The respective midpoint of the movement, with the path of the joint axis that also differs laterally, can be adjusted depending on individual anatomical conditions between the articulation points of the joint rods. The connection of the thigh and lower leg shells prevents lifting or slipping and rubbing by using independent orthosis joint mechanics. Each shell has a cutout dorsally in the vicinity of the fossa poplitea to permit pronounced flexure of the knee until the lower leg abuts the thigh.

SUMMARY OF THE INVENTION

The goal of the invention is to simplify the design of the knee joint orthosis described at the outset and to improve its operation further.

This goal is achieved according to the invention by virtue of the fact that the pivoting of at least one joint rod around its lower articulation point from the extended leg position into a knee bend takes place against a force opposing the pivoting, said force increasing up to a knee bend of about 30° to 40° and decreasing once more at approximately 90° flexure (seated position).

According the invention, therefore, at the beginning of the knee bend, in other words with pivoting of the joint rods, a bending resistance is developed. Bending of the joint rods is therefore possible only with a specific expenditure of force. This force, which is preferably adjustable, describes the distalizing pressure of the lower leg shell of the orthosis on the head of the tibia. To reinforce the anterior cruciform ligament function, the pressure mechanism is built up on the ventral parts of the tibia with a slight bending of the knee, reaches its maximum effect at 30° to 40°, and is reduced once again with the knee bent at 90°, in other words in the seated position. In this way, a favorable basic adjustment of the knee joint with injured cruciform ligaments is ensured in a slightly flexed position. It is precisely in this position that instabilities usually occur that lead to bending of the knee joint and are referred to as "giving way."

In a preferred embodiment, at least one joint rod is provided with a cam roller or the like that is urged by a spring elastic force against a cam mounted on the lower leg shell. The cam curve rises from a section that defines the approximately perpendicular position of the joint rod to a cam tip, which is located at a pivot angle of the joint rods of 30° to 40°. In a special design, it is advantageous for the joint rods each to consist of a tube that is guided displaceably lengthwise in a guide that forms the upper articulation point and surrounds a push rod mounted displaceably lengthwise in it, said push rod being fitted at its lower end with the cam roller and abutting a pretensioned spring with its upper end.

The bending movement of the natural knee joint is thus performed by a combination of shortening and deflection of the distance between the two articulation points, whose respective connection is made rigid, however. A mechanical joint, a joint axis, and therefore a mechanical pivot are no longer present.

The upper articulation point of the joint rods is located proximally with respect to the knee rotation area according to the invention and is preferably located 30 to 40 mm above the physiological knee pivot point. During flexion, this results in a backward displacement of the knee rods in the vicinity of the knee joint, so that even with pronounced flexion, tensioning of the orthosis by the cam mechanism is prevented.

The rotationally movable and lengthwise displaceable arrangement of the upper ends of the joint rods on the thigh shell ensures that the thigh and lower leg shells, throughout the entire movement involved in stretching and bending of the knee joint and during rotation, do not undergo any forced guidance or pretensioning. Instead, the orthosis merely produces a dorsalizing pressure on the anterior edge of the tibia. The nonphysiological forced guidance that occurs in other orthoses is avoided; good protection of the tibia against anterior translation is achieved.

For ease of assembly of the upper end of the joint rods on the upper articulation points associated with them, it is advantageous for the guide to be made in the form of a clip part that is approximately semicircular in cross section, in which clip part the tube forming the leg rod need merely be pressed.

To increase comfort it is advantageous for the spring elastic force pressing the cam roller against the cam to be provided with a built-in damper. Such a damper can use gas or oil and damp the movement of the push rods.

It would be possible to make the above-mentioned cams integral with the lower leg shells. However, from the standpoint of strength it appears advantageous for the cam to constitute the upper end of a rod rigidly connected with the lower leg shell.

It is advantageous for the two leg shells to have an internal lining to secure them in position. For this purpose, the orthosis can be designed using a two-shell technique with the outer shell constituting the shape of the orthosis according to the design while the inner shell is made as a cushion. The outer shell is preferably made by injection from a thermoplastic plastic so that reinforcing ribs and functional parts may be integrated. The cushioning advantageously consists of an embossed polyethylene foam. The flexibility of the orthosis shells is chosen so that they can adjust to changes in muscle volume caused by movement, without creating pressure points. Because of the novel connection of the two shells with one another, the orthosis shafts can be kept very short. As a result, a freedom of movement is produced that guarantees maximum flexion.

To prevent the upper shell from slipping downward because of the conical shape of the thigh, it is advantageous for the upper shell to have a condyle bed on its interior above the internal condyles of the femur. This can be made as a separate individually positionable pad that can be held in the desired position by a hook-and-loop fastener for example. It is also possible to make the corresponding internal area of the upper shell deformable, to enable it to adjust to individual conditions. A water or gas filling can be provided for this purpose that can also be made self-regulating.

The orthosis according to the invention offers the possibility of permitting individual anatomically determined movement patterns of the knee joint and allowing the buildup of force only at the front of the head of the tibia near the joint gap. In the case of the knee joint orthosis according to the invention, a fresh injury to the anterior cruciform ligament is valid as an indication for use, and in residual instabilities, use in sports and in non-surgically-treated cruciform ligament instabilities as a protection.

Additional features of the invention are the subject of the subclaims and will be described in greater detail in connection with further advantages of the invention with reference to embodiments.

BRIEF DESCRIPTION OF THE DRAWINGS

The drawings show two embodiments of the invention that serve as examples.

FIG. 4 shows the joint rod according to FIG. 3 in a modified embodiment;

FIG. 5 shows the joint rod according to FIG. 4 in the bent position; and

DETAILED DESCRIPTION OF THE PREFERRED EMBODIMENTS OF THE INVENTION

Figure 1:
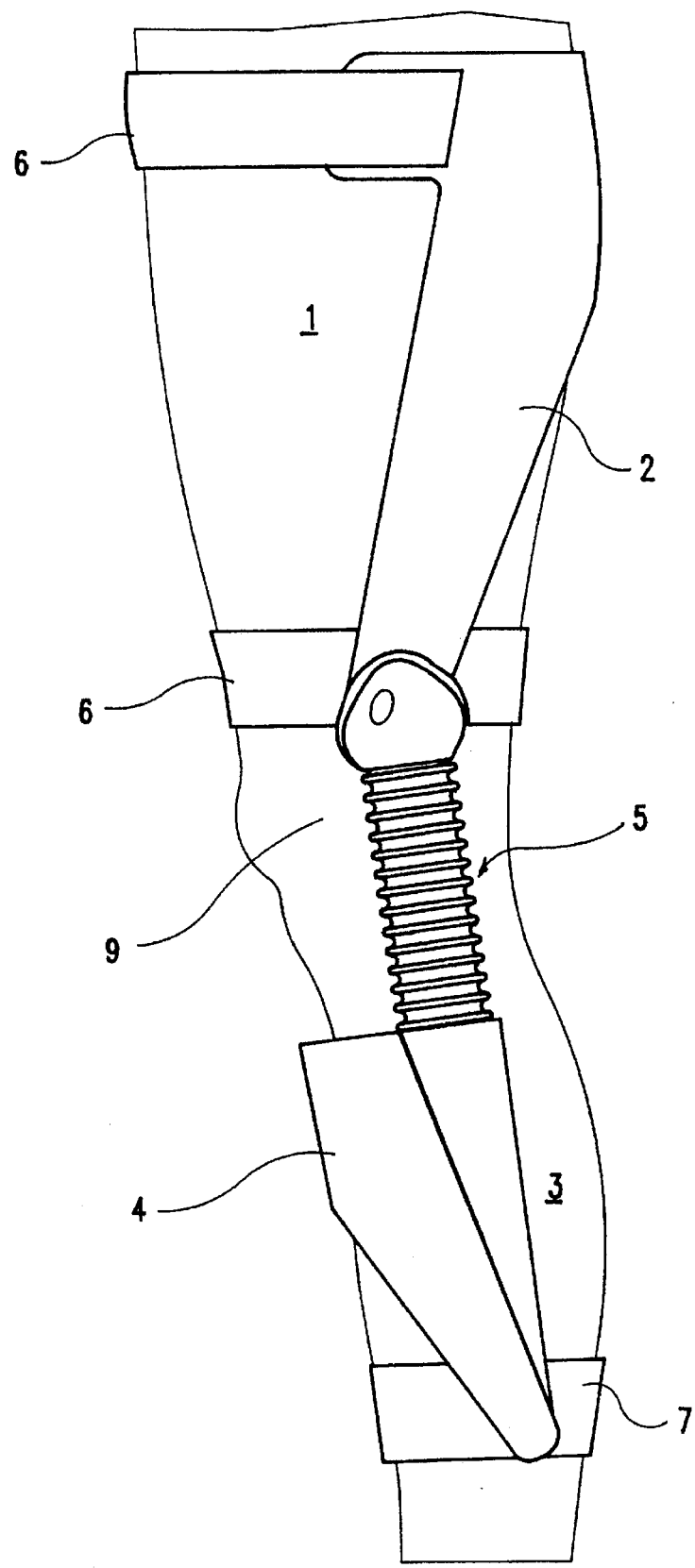
FIG. 1 is a side view of a knee joint orthosis mounted on an extended leg.
Figure 2:
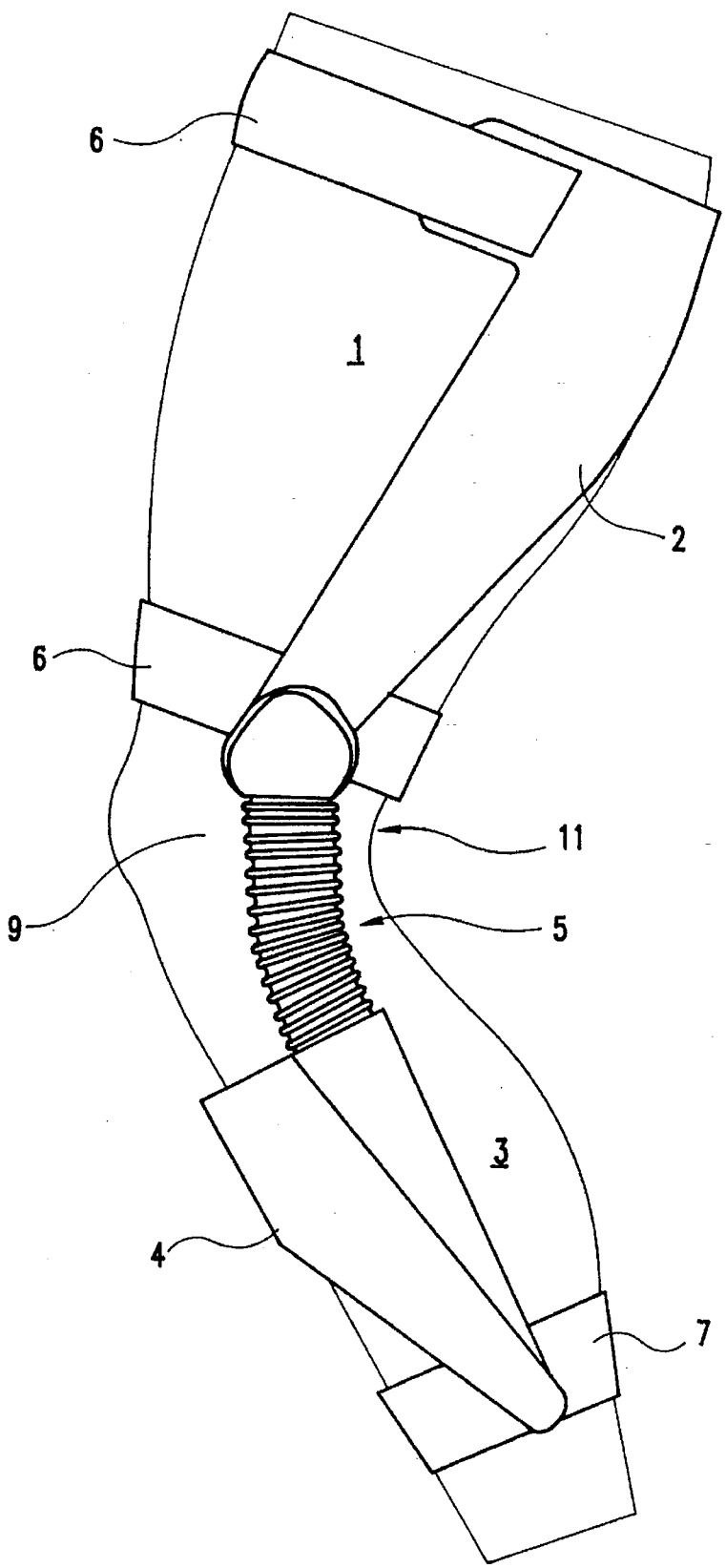
FIG. 2 is the same as FIG. 1 with the knee bent.

The knee joint orthosis shown comprises a thigh shell 2 to be mounted on thigh 1, a lower leg shell 4 to be mounted on lower leg 3, and two joint rods 5, said rods being located laterally opposite one another, approximately parallel with the leg extended, and connecting the two leg shells 2, 4 with articulation with one another. Thigh shell 2 surrounds thigh 1 dorsally, is open ventrally, and is closable in this area by hook-and-loop fasteners 6, while lower leg shell 4 surrounds lower leg 3 ventrally, is open dorsally, and is closable there by a hook-and-loop fastener 7.

Each joint rod 5 is connected by its upper end by an upper articulation point 8 with thigh shell 2 and at its lower end by a lower articulation point 10 with lower leg shell 4 in such fashion that the distance between the two articulation points 8, 10 decreases from a maximum with the leg extended to a minimum with the knee fully flexed. Upper articulation point 8 is located proximally with respect to knee rotation area 9, and therefore is located above the physiological knee pivot, while the lower articulation point 10 of joint rods 5 is in the vicinity of knee joint gap 11. The joint rods 5, which, when the leg is extended, lie in a plane perpendicular to the sagittal plane of the leg roughly centrally with respect to the leg, thus move behind knee rotation area 9 with increasing knee flexion. The perpendicular distance of upper articulation point 8 from the physiological knee pivot is preferably 30 to 40 mm. This rearward displacement of joint rods 5 during flexion, which is transmitted to lower leg shell 4, is an important effective principle of the orthosis.

Joint rod 5 consists of a tube 12 with its upper end guided displaceably lengthwise in a guide 13, which is formed as a clip part that is approximately semicircular in cross section, and also forms upper articulation point 8. Tube 12 surrounds a push rod 14 mounted displaceably lengthwise in it, said rod being fitted at its lower end with a cam roller 15 and abutting a pretensioned spring 16 with its upper end. The upper end of tube 12 is closed by an adjusting screw 17 that forms an axially adjustable counterbearing for spring 16, and whose head 17a simultaneously forms a stop opposite guide 13 (see FIGS. 4 and 5 in particular).

Figure 3:
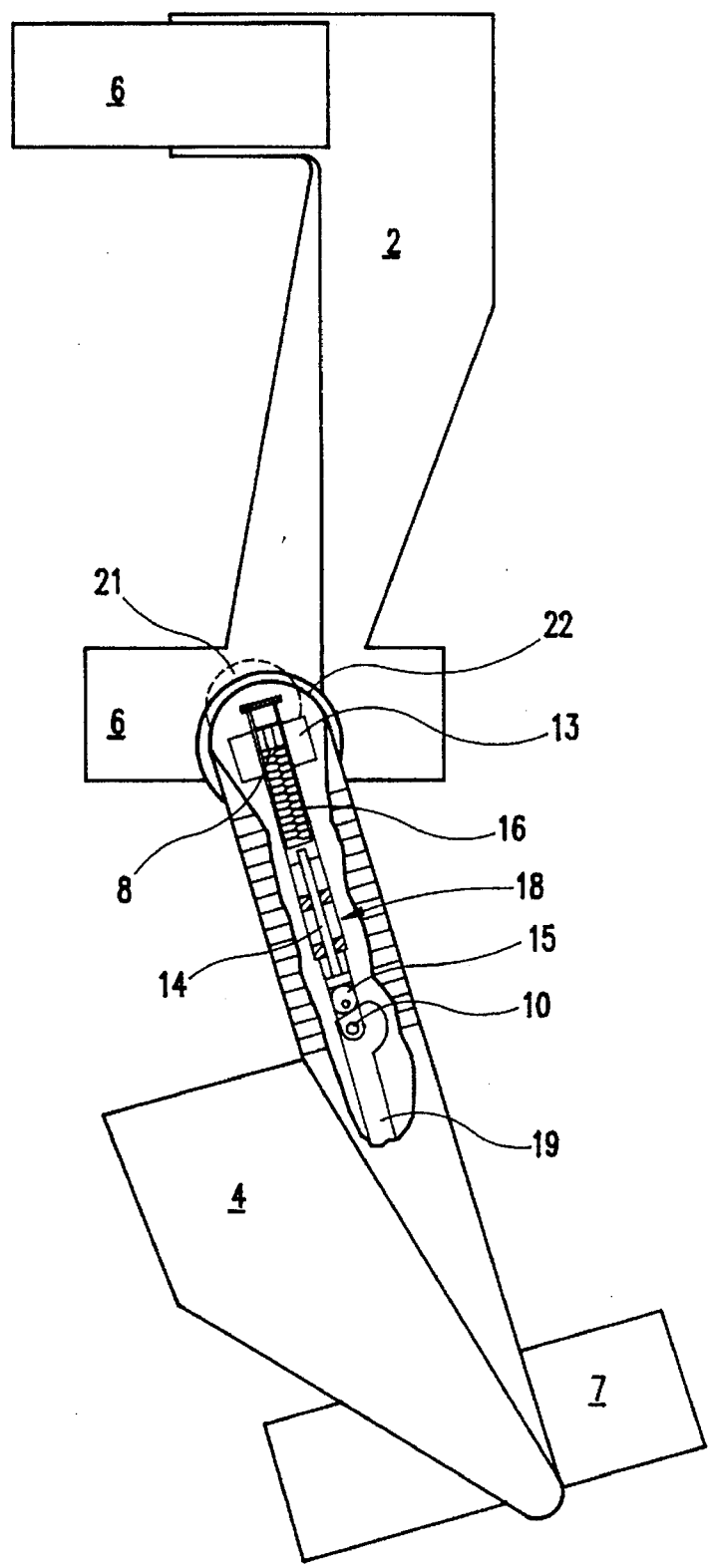
FIG. 3 is the same as FIG. 1 showing the orthosis alone with a lengthwise section through one joint rod.

In joint rods 5 shown in FIG. 3, spring 16 is provided with an integral damper 18 which uses oil or gas and controls the movement of push rods 14 in a damping fashion.

In the embodiments shown, the lower articulation point 10 of joint rods 5 is located on the upper end of a rod 19 that is rigidly connected with lower leg shell 4, forming a lower pivotal means. The free upper end of said rod being designed as a cam 20, against which cam roller 15 is urged by the force applied by spring 16. FIGS. 4 and 5 in particular show that the cam curve 20 rises from a section 20a that defines the approximately perpendicular position of joint rod 5 to a cam tip 20b which lies at a pivot angle α of joint rods 5 of 30° to 40°. Therefore, the spring 16, cam roller 15 and cam curve 20 comprise a biasing means.

Figure 6:
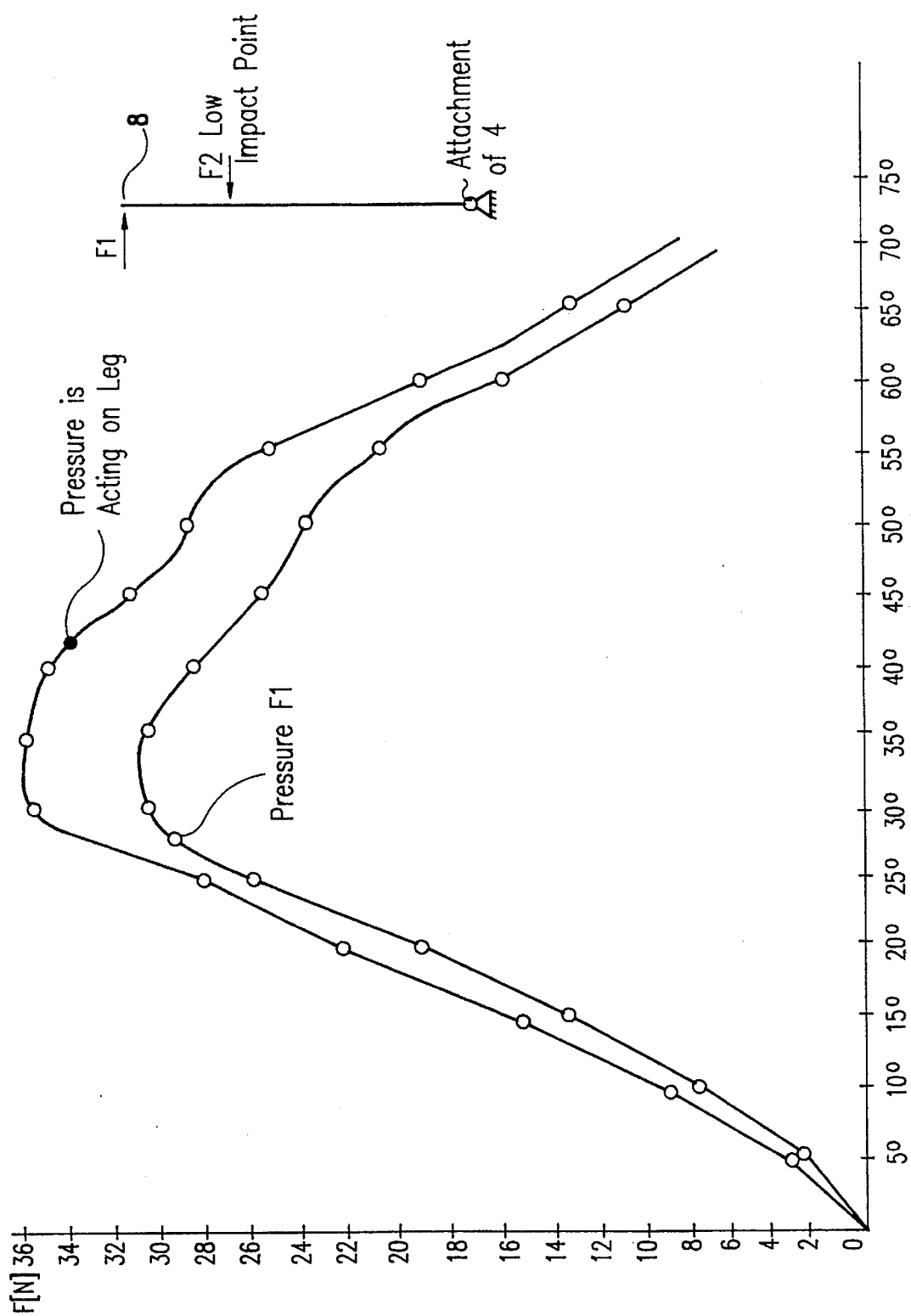
FIG. 6 is a diagram of the effective pressures.

The graph shown in FIG. 6 shows the pattern of spring force F, expressed in newtons, as a function of pivot angle α of joint rods 5, in other words as a function of the flexing of the knee beginning at the extended leg position with angle α=0. The lower curve shows the pattern of pressure F1 at upper articulation point 8 of guide 13 and the upper curve shows the pressure F2 acting on the leg engagement point (knee rotation area 9). This graph shows clearly that at the beginning of a knee bend and hence a pivoting of joint rods 5, an increasing bending resistance builds up; the bending of joint rods 5 is therefore possible only with a specific expenditure of force. This force which can be regulated with the aid of adjusting screw 17 is produced by the spring force and spring characteristic of spring 16, the shape of cam 20, and the lever ratio that is defined by articulation points 8 and 10.

Upper leg shell 2 can have a condyle bed 21 on its interior above the interior condyles of the femur, said bed in the representation shown in FIG. 3 being located slightly behind the circular area 2, and can be made in the form of a separate individually positionable pad or can be formed by a deformable area.

To hold them in position, the two leg shells 2, 4 are provided with an internal lining, not shown in greater detail in the drawing.

While the invention has been described in terms of its preferred embodiments, those skilled in the art will recognize that the invention can be practiced with modification within the spirit and scope of the appended claims.

We claim:

1. A knee joint orthosis, comprising:
   a thigh shell attachable to a thigh;
   a lower leg shell connected to said thigh shell and attachable to a lower leg;
   a pair of joint rods comprising a first joint rod and a second joint rod laterally opposing said first joint rod, said joint rods connecting said thigh shell to said lower leg shell in an articulated manner for allowing pivoting of said joint rods relative to said thigh shell and said lower leg shell, wherein when a leg is extended said joint rods are located within a plane perpendicular to a sagittal plane of said leg and are approximately parallel to said leg, wherein as a knee of said leg bends said joint rods move behind a fulcrum of said knee;

upper pivotal means for connecting each of said joint rods to said thigh shell and lower pivotal means for operatively connecting each of said joint rods to said lower leg shell;

wherein a distance between said upper pivotal means and said lower pivotal means has a maximum value when said leg is extended and a minimum value when said knee is completely bent;

said upper pivotal means each comprising a guide, wherein an upper section of each of said joint rods is slidably positioned within said guide; and biasing means, connected to at least one joint rod of said joint rods, for providing a bias opposing pivoting of said at least one joint rod relative to at least one of said thigh shell and said lower leg shell during knee bending, said biasing means providing an opposing bias which varies corresponding to a joint angle varying, said joint angle comprising an angle of an axis of said thigh shell to an axis of said lower leg shell, wherein said bias has a first force value when said joint angle is 0°, a second three value when said joint angle is approximately 30°–40° and a third force value when said joint angle is 90°, wherein said second force value is greater than said first force value and said second force value is greater than said third force value.

2. A knee joint orthosis according to claim 1, wherein said biasing means includes:

a spring member having an axis and two opposing ends; and an adjusting screw abutting one of said ends comprising an axially adjustable counterbearing for said spring member.

3. A knee joint orthosis, comprising:

a thigh shell attachable to a thigh;

a lower leg shell connected to said thigh shell and attachable to a lower leg;

a pair of joint rods comprising a first joint rod and a second joint rod laterally opposing said first joint rod, said joint rods connecting said thigh shell to said lower leg shell in an articulated manner for allowing pivoting of said joint rods relative to said thigh shell and said lower leg shell, wherein when a leg is extended said joint rods are located within a plane perpendicular to a sagittal plane of said leg and are approximately parallel to said leg, wherein as a knee of said leg bends said joint rods move behind a fulcrum of said knee;

upper pivotal means for connecting each of said joint rods to said thigh shell and lower pivotal means for operatively connecting each of said joint rods to said lower leg shell;

wherein a distance between said upper pivotal means and said lower pivotal means has a maximum value when said leg is extended and a minimum value when said knee is completely bent;

said upper pivotal means each comprising a guide, wherein an upper section of each of said joint rods is slidably positioned within said guide; and biasing means, connected to at least one joint rod of said joint rods, for providing a bias opposing pivoting of said at least one joint rod relative to at least one of said thigh shell and said lower leg shell during knee bending, said biasing means providing an opposing bias which varies corresponding to a joint angle varying, said joint angle comprising an angle of an axis of said thigh shell to an axis of said lower leg shell, wherein said bias has a first force value when said joint angle is 0°, a second force value when said joint angle is approximately 30°–40° and a third force value when said joint angle is 90°, wherein said second force value is greater than said first force value and said second force value is greater than said third force value, wherein said biasing means includes a cam roller, said cam roller being urged, by said biasing means, against a cam connected to said lower leg shell.

4. A knee joint orthosis according to claim 3, wherein said cam includes a first cam contour, said first cam contour including an incline extending from a starting point to a cam peak, said starting point being a first point on said cam where said cam roller contacts said cam when said leg is extended, said cam peak being a second point on said cam where said cam roller contacts said cam when said joint angle is approximately 30°–40°.

5. A knee joint orthosis according to claim 3, wherein said at least one joint rod includes a push rod having a lower end connected to said cam roller and an upper end abutting said biasing means.

6. A knee joint orthosis according to claim 5, wherein said push rod is mounted displaceably and lengthwise in a tube, said tube having an upper end located within said guide.

7. A knee joint orthosis according to claim 6, wherein said upper end of said tube includes an adjusting screw closing said upper end, said screw comprising an axially adjustable counterbearing for said biasing means.

8. A knee joint orthosis according to claim 7, wherein said adjusting screw includes a head located above said guide and comprises a stop for stopping further slidable lengthwise movement of said joint rods within said guide.

9. A knee joint orthosis according to claim 1, wherein said biasing means includes an integrated damper.

10. A knee joint orthosis according to claim 1, wherein said guide has an approximately semicircular cross section.

11. A knee joint orthosis according to claim 1, wherein said thigh shell is for surrounding said thigh dorsally and includes a first hook-and-loop fastener for ventrally closing said thigh shell, said lower leg shell being for surrounding said lower leg ventrally and including a second hook-and-loop fastener for dorsally closing said lower leg shell.

12. A knee joint orthosis according to claim 1, further comprising a condyle bed attached to an interior of said thigh shell in a region opposing said guide.

13. A knee joint orthosis according to claim 12, wherein said condyle bed comprises a separate, individually positionable pad.

14. A knee joint orthosis according to claim 12, wherein said condyle bed comprises a deformable area of said interior of said thigh shell.

15. A knee joint orthosis according to claim 1, wherein said thigh shell and said lower leg shell each have an internal lining for holding said thigh shell and said lower leg shell in position on said leg.

* * * * *